United States Patent [19]

Nakamura

[11] Patent Number: 5,231,279
[45] Date of Patent: Jul. 27, 1993

[54] AUTOMATIC FOCUSING MECHANISM FOR AN OPERATION MICROSCOPE HAVING AN ORIGIN RETURNING MECHANISM

[75] Inventor: Katsushige Nakamura, Tokyo, Japan
[73] Assignee: Kesanori Sahara, Fuchu, Japan
[21] Appl. No.: 897,478
[22] Filed: Jun. 12, 1992

[30] Foreign Application Priority Data

Dec. 25, 1991 [JP] Japan .................. 3-342578

[51] Int. Cl.⁵ .............................. G01J 1/20
[52] U.S. Cl. .................. 250/201.2; 250/201.3
[58] Field of Search ............... 250/201.3, 201.2, 205, 250/204; 359/380, 381, 383, 384

[56] References Cited

U.S. PATENT DOCUMENTS

| | | | |
|---|---|---|---|
| 3,830,571 | 8/1974 | Imai et al. | 250/201.2 |
| 4,447,717 | 5/1984 | Nohda | 250/201.4 |
| 4,725,720 | 2/1988 | Sawada et al. | 250/205 |

Primary Examiner—David C. Nelms
Assistant Examiner—Que T. Le
Attorney, Agent, or Firm—Beveridge, DeGrandi, Weilacher & Young

[57] ABSTRACT

The invention relates to an automatic focusing mechanism for an operation microscope. In the apparatus in accordance with the invention, when the position and angle of the operation microscope is altered by the operator, a constant moving margin is always secured so that the automatic focusing mechanism has sufficient room to perform the focusing function. This is accomplished by setting an optional origin position within the moving range of the drive objective section of the operation microscope. When the operation microscope is brought to a free condition by a switch section, a driver mechanism operates so as to return the drive objective section to the location of the origin position. Thus, when the position and angle of the microscope is altered, a constant moving margin of the drive objective section is always maintained. Thus, the location of the drive objective section always has sufficient room to perform the automatic focusing function.

14 Claims, 2 Drawing Sheets

AUTOMATIC FOCUSING MECHANISM FOR AN OPERATION MICROSCOPE HAVING AN ORIGIN RETURNING MECHANISM

BACKGROUND OF THE INVENTION

1. Field of the Invention

The present invention relates to automatic focusing mechanisms for operation microscopes and, particularly, to an automatic focusing mechanism for an operation microscope, having an origin returning function.

2. Description of the Prior Art

Local operation of an affected or diseased part in a cerebral surgical operation and a heart surgical operation is executed while observing the affected part by an operation microscope, and is generally called "microsurgery". FIG. 2 of the attached drawings shows an example of the use of such conventional operation microscope (refer to Japanese Patent Laid-Open No. SHO 64-56409, id est, U.S. Pat. No. 4,881,709).

The reference numeral 1 denotes an operation microscope. The operation microscope 1 is mounted on a depending arm 2 of a stand apparatus (not shown), whereby the operation microscope 1 is movable in any direction including front and rear directions, upper and lower directions and left- and right-hand directions, and an observation angle $\theta$ can also be altered freely.

That is, a switch section 5, which is provided on a grip section 4 of an operating arm 3, is depressed whereby the operation microscope 1 is brought to a free condition as if the operation microscope 1 floats in the air. Accordingly, an operator D sets the operation microscope 1 to a desired location or position while the switch section 5 is depressed. Then, when the operator D leaves or detaches his hand from the switch section 5, an electromagnetic clutch (not shown) operates so that the operation microscope 1 is brought to such a condition as to be locked at its position.

When the operation microscope 1 is fixed to a predetermined position, an objective lens (optical element) 7 moves along a focus control direction F by an automatic focusing mechanism 6 which is incorporated in the operation microscope 1, so that the focus is taken to an observation target point X on a patient P.

FIG. 3 shows a structure or construction of the automatic focusing mechanism 6. The reference numeral 8 denotes a support section by which control of the objective lens 7 is executed. That is, within the support section 8, the automatic focusing mechanism 6 is provided which comprises upper- and lower-side limit switches 9 and 10, a drive objective section 11 in interlocking relation to the objective lens 7, and drive means 12 for reciprocating the drive objective section 11 within a moving extent or range E between the upper-side limit switch 9 and the lower-side limit switch 10. The drive means 12 moves the drive objective section 11 along the focus control direction F, whereby the objective lens 7 is also moved in interlocking relation thereto, thereby executing zoom regulation or adjustment.

That is, a foot switch 12a, which is located at feet of the operator D, is connected to the drive means 12. After the operation microscope 1 has been brought to the lock condition (a condition under which a hand is released or detached from the switch section 5), the foot switch 12a is depressed whereby the drive objective section 11 is moved toward the upper limit switch 9 or toward the lower limit switch 10 so that zoom adjustment of a field of view can be executed.

In the case of such conventional automatic focusing mechanism for the operation microscope, however, a problem illustrated in FIG. 4 arises. That is, after the switch section 5 has been depressed to bring the operation microscope 1 to a free condition, when the operation microscope 1 is moved to a point different from the observation target point X which has been seen until now, and when the operation microscope 1 is brought to a locked condition at the point to see or look the point, a problem illustrated in FIG. 4 arises.

That is, the operator D depresses the switch section 5 during operation to alter a position of the operation microscope 1 several times, and operates the foot switch 12a every position to execute zoom adjustment. For this reason, the operator D does not accurately grasp at what position within the moving range E the drive objective section 11 is located. Accordingly, as shown in FIG. 4, it is desired for the operator D to operate the foot switch 12a thereby moving the objective lens 7 (drive objective section 11) downwardly correspondingly to EX. Since, however, a downwardly moving margin E1 of the drive objective section 11 has only a small amount of room left, there may occur a situation that desired zoom adjustment cannot be executed.

SUMMARY OF THE INVENTION

This invention has been done in view of the above-described prior art, and it is an object of the invention to provide an automatic focusing mechanism for an operation microscope, which is capable of preventing the aforesaid situation from occurring.

In order to achieve the above-described object, an automatic focusing mechanism for an operation microscope, according to the invention, is arranged such that an optional origin is set within a moving range of a drive objective section, and when the operation microscope is brought to a free condition by the switch section, the drive section returns the drive objective section to the origin position.

Each time the operation microscope is brought to the free condition by the switch section, the drive objective section is returned to the origin which is set within the moving range. Accordingly, while there is a small amount of movement needed within the moving margin of the drive objective section, the position and the angle of the operation microscope are not altered. Thus, when the position and the angle of the operation microscope are altered, a constant moving margin is always secured. Accordingly, it is possible to sufficiently exhibit a focusing function of the automatic focusing mechanism.

DESCRIPTION OF THE PREFERRED EMBODIMENTS

Figure 1:
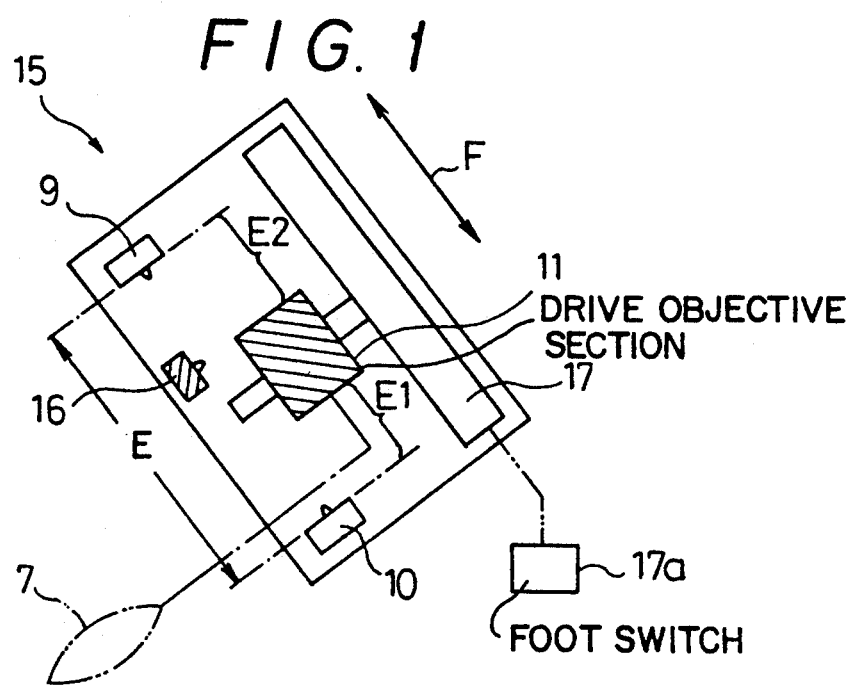
FIG. 1 is a schematic view showing an automatic focusing mechanism for an operation microscope, according to an embodiment of the invention.

A preferred embodiment of the invention will hereunder be described with reference to FIG. 1. In this connection, the same or like reference numerals are applied to parts and components which are common to the conventional arrangement, and the description of the same or like reference numerals will be omitted to avoid duplication. Accordingly, the embodiment will hereunder be described with reference to FIG. 2 which shows the conventional arrangement.

An automatic focusing mechanism 15 according to the embodiment sets an origin switch 16 within a moving range or region E between an upper-side limit switch 9 and a lower-side limit switch 10. Further, the reference numeral 17a denotes a foot switch.

Figure 2:
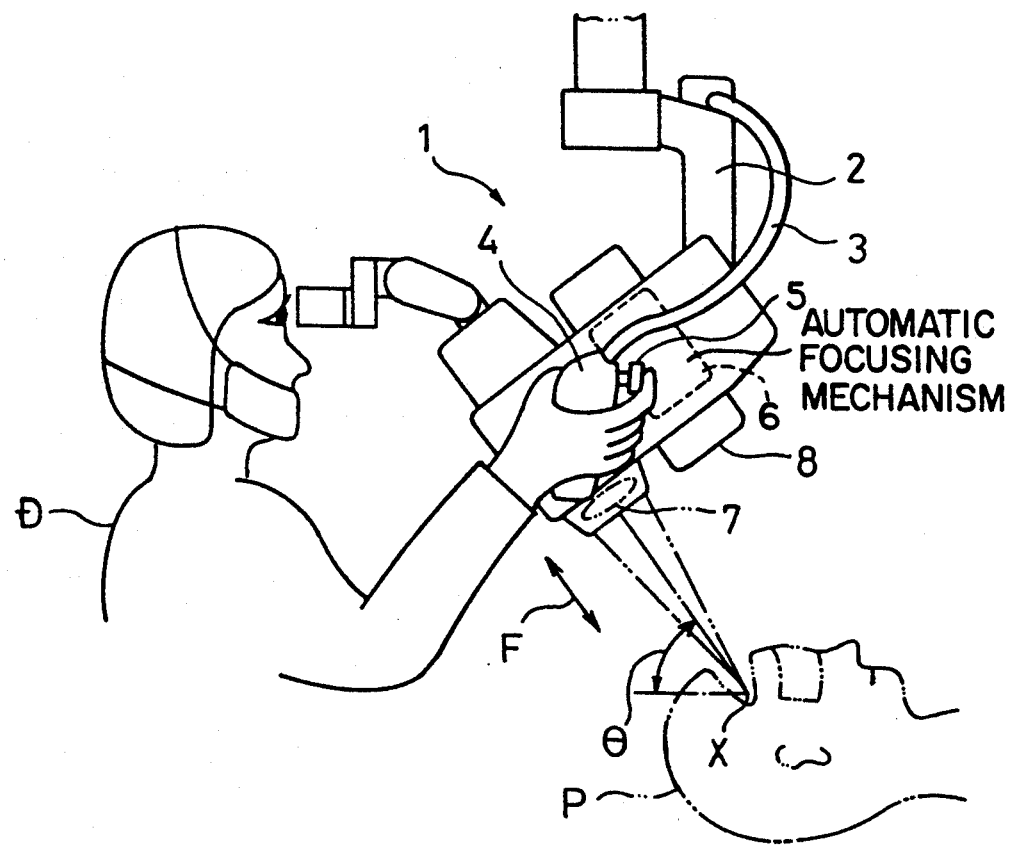
FIG. 2 is a side elevation showing an operational example of an operation microscope which is provided with a conventional automatic focusing mechanism.
Figure 3:
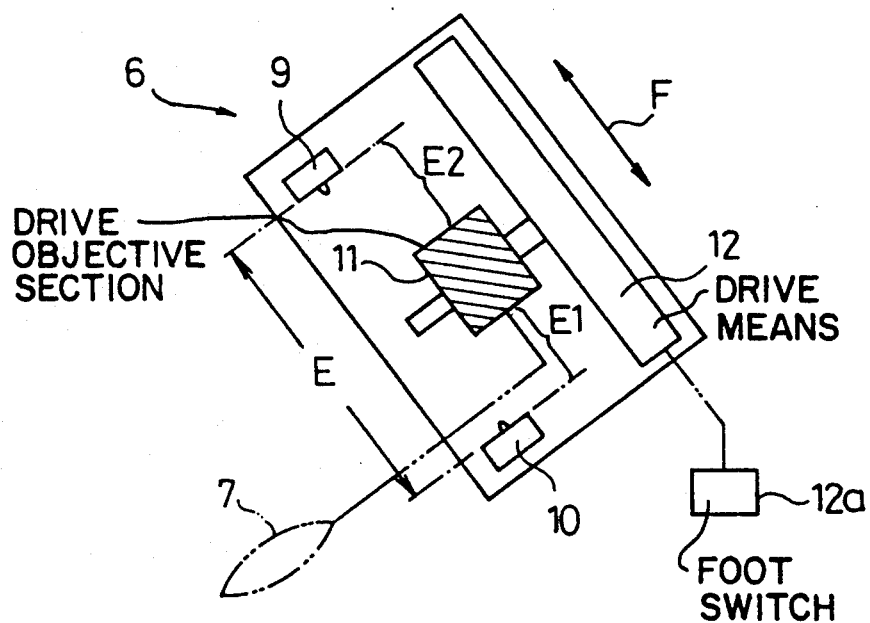
FIG. 3 is a schematic view showing the conventional automatic focusing mechanism.
Figure 4:
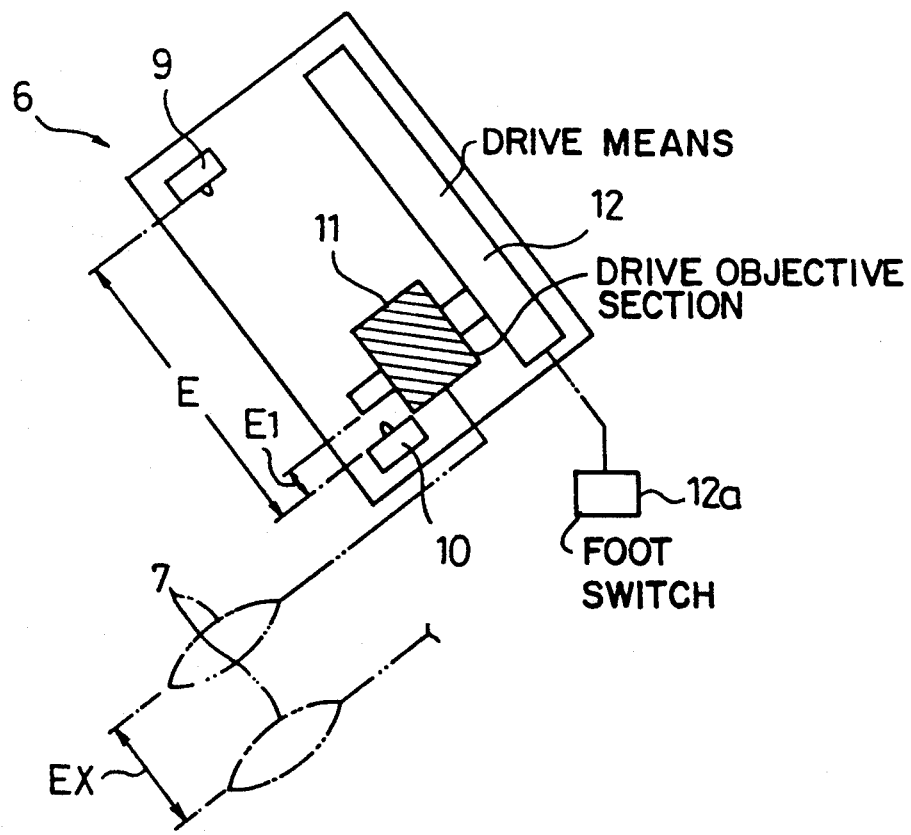
FIG. 4 is a schematic view corresponding to FIG. 3, showing a small condition under which a moving margin is left.

In this embodiment, as will be easy to understand with reference to FIG. 2, when the switch section 5 is depressed in order to alter a position and an angle of the operation microscope 1, so that the operation microscope 1 is brought to a free condition, drive means 17 executes an origin returning operation. That is, at the time the switch section 5 is depressed, in the case where a drive objective section 11 is located between the upper-side limit switch 9 and the origin switch 16, the drive objective section 11 is lowered so that the position of the drive objective section 11 is aligned with the origin switch 16. Further, in the case where the drive objective section 11 is located between the lower-side limit switch 10 and the origin switch 16, the drive objective section 11 is raised or moved upwardly to align the position of the drive objective section 11 with the origin switch 16.

In this manner, as will be easy to understand with reference to FIG. 2, in the case where the switch section 5 is depressed in order to alter the position and the angel of the operation microscope 1, the drive objective section 11 is surely returned to the position of the origin switch 16. Accordingly, the drive objective section 11 is brought to a condition that moving margins E2 and E1 can sufficiently be secured at the upper side and the lower side, respectively. Thus, when the position or the angle of the operation microscope 1 is altered so that portions of the patient P in the neighborhood of the observation point X are again observed, sufficient moving margins E1 and E2 can be secured at the upper side and the lower side of the drive objective section 11, respectively. Accordingly, the focusing function is not impeded by insufficiency of the moving margins.

The set position of the origin switch 16 is movable within the moving range E, and it is not necessarily required that the origin switch 16 is set to a central position of the moving range E. It is sufficient that the origin switch 16 is set to a desired location. That is, there is a personal equation for the operator D how to handle the operation microscope 1, and the handling of the operation microscope 1 is different depending upon operation locations. Accordingly, the position of the origin switch 16 is decided or determined in view of such various conditions. That is, in the case where there is a tendency (necessity) that a focal point of the operation microscope 1 is once taken to a shallow location and, then, the focal point is gradually moved to a deep section, the origin switch 16 is set relatively to a higher position so that the lower-side moving margin E1 is sufficiently secured. Also in this embodiment, the lower moving margin E1 is provided slightly longer than the upper moving margin E2. Furthermore, in the case where there is the opposite or reversed tendency (necessity), the origin switch 16 is set to a slightly lower position so that the upper moving margin E2 becomes large or is enlarged.

Since the automatic focusing mechanism 15 according to the embodiment does not injure the original focus control function, there can be produced the following additional advantages.

A) It is not required or is unnecessary for the operator D to mind or care of the position of the drive objective section 11 so that there is an additional advantage that the operator D can give undivided attention to the operation.

B) In the case of a so-called "point lock" in which is focal-point position of the objective lens 7 is in agreement with a center point of movement of the operation microscope 1, if the position of the origin switch 16 is beforehand in agreement with the focal-point position of the objective lens 7, the focal-point position of the objective lens 7 is in agreement with the center point of movement of the operation microscope 1 each time the switch section 5 is depressed, so that point-lock operation of the operation microscope 1 can be executed always under the best condition.

C) If the position of the origin switch 16 is beforehand in agreement with an optimum center-of-gravity position of a support apparatus (stand apparatus) for the operation microscope 1, stability of the support apparatus per se increases, and a force at the time the support apparatus is operated to alter the position of the heavy operation microscope 1 is uniformized so that an attempt can be made to accurately execute operation of the operation microscope 1, and a fatigue of the operator in the case where the operation is executed for a long period of time is reduced. That is, if an attempt is not made at a weight balance of the support apparatus, a force required for the operation is largely different depending upon a direction to be operated. Accordingly, it is difficult to execute the positioning operation of the operation microscope 1. According to the invention, however, there is no such fear.

In connection with the above, an operation section of the drive means 17 has been described for example as the foot switch 17a. However, the invention should not be limited to the foot switch 17a.

The automatic focusing mechanism for the operation microscope, according to the invention, has the contents as described above. Each time the operation microscope is brought to the free condition by the switch section, the drive objective section is returned to the origin which is set within the moving range. Accordingly, the position and the angle of the operation microscope are not altered, with a condition that there are small movements needed within the moving margins of the drive objective section. Thus, since, when the position and the angle of the operation microscope are altered, a constant moving margin is always secured, it is possible to sufficiently exhibit the focusing function of the automatic focusing mechanism.

What is claimed is:

1. An automatic focusing mechanism for an operation microscope, in which the automatic focusing mechanism is supported so as to be movable to a position by a stand apparatus, and wherein the operation microscope is switchable between a locked condition and a free condition by operation of a switch section, comprising:

a drive objective section in an interlocking relation to an optical element of the operation microscope; a drive means for moving said drive objective section along a focal-point control direction, within a predetermined moving range, in order to control a focal distance, and means for setting an optional origin position within the moving range of said drive objective section, such that when the operation microscope is brought to the free condition by said switch section, said drive means returns said drive objective section to said origin position.

2. An automatic focusing mechanism according to claim 1, wherein the optical element includes an objective lens.

3. An automatic focusing mechanism according to claim 1, further comprising a foot switch for activating the drive means.

4. An automatic focusing mechanism according to claim 1, further comprising:

an upper-side limit switch to limit movement of the drive objective section in the focal point control direction;

a lower-side limit switch to limit movement of the drive objective section in the focal point control direction;

wherein the lower-side limit switch and the upper-side limit switch define the moving range of the drive objective section.

5. An automatic focusing mechanism for an operation microscope, wherein the operation microscope is movable between a free condition and a locked condition, comprising:

a drive objective section in an interlocking relation with an optical element of the operation microscope, wherein the drive objective section is movable within a moving range along a focal point control direction;

an upper-side limit switch to limit movement of the drive objective section in the focal point control direction;

a lower-side limit switch to limit movement of the drive objective section in the focal point control direction;

wherein the lower-side limit switch and the upper-side limit switch define the moving range of the drive objective section;

a drive means for moving the drive objective section within the moving range; and means for setting an origin position within the moving range of the drive objective section, such that when the operation microscope is brought to the free condition, the drive means returns the drive objective section to the origin position.

6. An automatic focusing mechanism according to claim 5, wherein the optical element includes an objective lens.

7. An automatic focusing mechanism according to claim 5, wherein the means for setting the origin position is a switch.

8. An automatic focusing mechanism according to claim 5, further comprising a foot switch for activating the drive means.

9. An operation microscope, comprising:

a stand apparatus for positioning an optical element of the operation microscope, wherein at least a portion of the operation microscope is switchable between a locked condition and a free condition;

a switch section for switching the portion of the operation microscope between the locked condition and the free condition;

a drive objective section in an interlocking relation with the optical element, wherein the drive objective section is movable within a moving range along a focal point control direction;

a drive means for moving the drive objective section within the moving range; and means for setting an origin position within the moving range of the drive objective section, such that when the operation microscope is brought to the free condition by operation of the switch section, the drive means returns the drive objective section to the origin position.

10. An operation microscope according to claim 9, wherein the optical element includes an objective lens.

11. An operation microscope according to claim 9, wherein the means for setting the origin position is a switch.

12. An operation microscope according to claim 9, further comprising a foot switch for activating the drive means.

13. An operation microscope according to claim 9, wherein the switch section includes a hand grip section.

14. An operation microscope according to claim 9, further comprising:

an upper-side limit switch to limit movement of the drive objective section in the focal point control direction;

a lower-side limit switch to limit movement of the drive objective section in the focal point control direction;

wherein the lower-side limit switch and the upper-side limit switch define the moving range of the drive objective section.

* * * * *